United States Patent [19]

Török et al.

[11] 4,410,697
[45] Oct. 18, 1983

[54] PROCESS FOR THE PREPARATION OF N-ARYL-N'-(MONO- OR DI SUBSTITUTED)-UREA DERIVATIVES

[75] Inventors: Sándor Török; Lajos Vörösházy; Péter Galambos; Iván Daróczi; Zoltán Orményi, all of Budapest, Hungary

[73] Assignee: Reanal Finomvegyszergyár, Hungary

[21] Appl. No.: 299,030

[22] PCT Filed: Jan. 23, 1981

[86] PCT No.: PCT/HU81/00003

§ 371 Date: Aug. 28, 1981

§ 102(e) Date: Aug. 28, 1981

[87] PCT Pub. No.: WO81/02156

PCT Pub. Date: Aug. 6, 1981

[30] Foreign Application Priority Data

Jan. 25, 1980 [HU] Hungary ................................. 157/80
Jan. 25, 1980 [HU] Hungary ................................. 158/80

[51] Int. Cl.³ .................... C07C 127/19; C07C 127/17
[52] U.S. Cl. ..................................... 544/165; 544/167;
546/330; 546/337; 564/48; 564/49; 564/50;
564/51; 564/52; 564/53; 564/54; 260/453 RW;
562/437; 562/439
[58] Field of Search .................... 564/48, 49, 50, 51,
564/52, 53, 54; 544/165, 167; 546/330, 337;
260/453 RW; 562/437, 439

[56] References Cited

U.S. PATENT DOCUMENTS 3,555,086  1/1971  Weis et al. ....................... 564/48 X

FOREIGN PATENT DOCUMENTS 2617918  10/1976  Fed. Rep. of Germany ........ 564/48

OTHER PUBLICATIONS

Crosby et al., JACS 76, pp. 4458–4463, (1954).
Schuller et al., JACS 75, pp. 3425–3428, (1953).

*Primary Examiner*—Thomas A. Waltz
*Attorney, Agent, or Firm*—Keil & Witherspoon

[57] ABSTRACT

The invention relates to a new method for the preparation of N-aryl-N'-(mono- or disubstituted)-urea derivatives having the general formula (I),

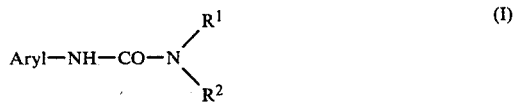

wherein
Aryl is an optionally substituted phenyl group, and
$R^1$ and $R^2$ each stand for an optionally substituted alkyl, cycloalkyl, alkoxy or phenyl group, or
$R^1$ and $R^2$ may form, together with the adjacent nitrogen atom, a nitrogen-containing heterocyclic group which may contain a further hetero atom, or
one of $R^1$ and $R^2$ may also stand for hydrogen,
with the proviso that if one of $R^1$ and $R^2$ is an optionally substituted phenyl group, the other may represent only hydrogen atom or an optionally substituted alkyl or alkoxy group, by reacting a carbamate of the general formula (II) with an amine of the general formula (III),

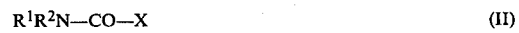

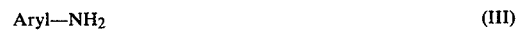

or a carbamate of the general formula (IV) with an amine of the general formula (V),

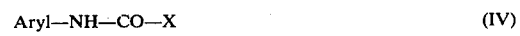

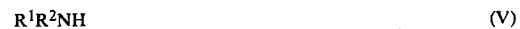

wherein $R^1$, $R^2$ and Aryl are as defined above and X is a lower alkoxy, phenoxy or substituted phenoxy group, in the presence of a tertiary amine catalyst. According to the invention a tertiary alkylamine containing altogether at least 6 carbon atoms and minimum one alkyl chain with at least 4 carbon atoms or a mixture of such tertiary alkylamines is applied as catalyst.

5 Claims, No Drawings

PROCESS FOR THE PREPARATION OF N-ARYL-N'-(MONO- OR DI SUBSTITUTED)-UREA DERIVATIVES

The invention relates to a new process for the preparation of N-aryl-N'-(mono- or disubstituted)-urea derivatives having the general formula (I),

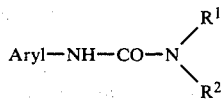

wherein
Aryl is an optionally substituted phenyl group, and
$R^1$ and $R^2$ each stand for an optionally substituted alkyl, cycloalkyl, alkoxy or phenyl group, or
$R^1$ and $R^2$ may form, together with the adjacent nitrogen atom, a nitrogen-containing heterocyclic group which may contain a further hetero atom, or one of $R^1$ and $R^2$ may also stand for hydrogen,
with the proviso that if one of $R^1$ and $R^2$ is an optionally substituted phenyl group, the other may represent only hydrogen atom or an optionally substituted alkyl or alkoxy group.

The phenyl group represented by "Aryl" may bear as optional substituents preferably one or more halogen atoms, nitro groups(s), lower alkyl group(s), lower alkoxy group(s), trihalo-lower alkyl group(s), lower alkylthio group(s) or a phenoxy group optionally substituted with the groups listed in this paragraph.

$R^1$ and $R^2$ may represent as alkyl or alkoxy group preferably a group of 1 to 4 carbon atoms, whereas the cycloalkyl groups represented by $R^1$ or $R^2$ contain preferably 5 to 8 carbon atoms. These groups may bear optionally e.g. the following substituents: hydroxy group, carboxy group, alkyl group, alkenyl group, alkynyl group, alkoxy group, phenyl group, substituted phenyl group or heteroaryl group. Of the nitrogen-containing heterocyclic groups represented by $R^1R^2N$— the morpholino group is preferred.

The compounds of the general formula (I) are biologically active or can be converted into biologically active substances.

Some representatives of the compounds having the general formula (I), such as those wherein Aryl is as defined above, $R^1$ is hydrogen or an optionally substituted alkyl or cycloalkyl group and $R^2$ is an optionally substituted alkyl or alkoxy group, exert pesticidal, primarily herbicidal effects (see e.g. R. Wegler: Chemie der Pflanzenschutz- und Schädlingsbekämpfungsmittel, Springer Verlag, Berlin-Heidelberg-New York, 1970, pp. 241 to 255). Other compounds of the general formula (I), such as N-(4-nitrophenyl)-N'-(3'-pyridylmethyl)-urea (pyrinuron), can be applied as rodenticidal agents. Further representatives of the compounds having the general formula (I), such as those wherein one of $R^1$ and $R^2$ is hydrogen and the other is an optionally substituted phenyl group, are pharmaceutically active or can be applied as intermediates in the preparation of pharmaceutically active agents.

Preferred representatives of the compounds having the general formula (I) are as follows:

N-phenyl-N',N'-dimethyl-urea(fenuron), a herbicidal substance,

N-phenyl-N'-(2-methylcyclohexyl)-urea(siduron), a herbicidal substance,
N-(4-chlorophenyl)-N',N'-dimethyl-urea(monuron), a herbicidal substance,
N-(3,4-dichlorophenyl)-N'-methyl-N'-butyl-urea(neburon), a herbicidal substance,
N-(3,4-dichlorophenyl)-N',N'-dimethyl-urea(diuron), a herbicidal substance,
N-(3-trifluoromethylphenyl)-N',N'-dimethyl-urea(-fluomethuron), a herbicidal substance,
N-(3-chloro-4-trifluoromethylphenyl)-N',N'-dimethyl-urea, a herbicidal substance,
N-(3-chloro-4-methylphenyl)-N',N'-dimethyl-urea(-chlortoluron), a herbicidal substance,
N(4-isopropylphenyl)-N',N'-dimethyl-urea(isoproturon), a herbicidal substance,
N-(3,4-dichlorophenyl)-carbamoyl-morpholine, a herbicidal substance,
N-(3-chloro-4-bromophenyl)-carbamoyl-morpholine, a herbicidal substance,
N-(3-chlorophenyl)-carbamoyl-morpholine, a herbicidal substance,
N-(4-chlorophenyl)-carbamoyl-morpholine, a herbicidal substance,
N-(3-chloro-4-methoxyphenyl)-N',N'-dimethyl-urea(-metoxuron), a herbicidal substance,
N-[4-(4-chlorophenoxy)-phenyl]-N',N'-dimethyl-urea(-chloroxuron), a herbicidal substance,
N-(4-chlorophenyl)-N'-methyl-N'-methoxy-urea(-monolinuron), a herbicidal substance,
N-(4-bromophenyl)-N'-methyl-N'-methoxy-urea(metobromuron), a herbicidal substance,
N-(3,4-dichlorophenyl)-N'-methyl-N'-methoxy-urea(-linuron), a herbicidal substance,
N-(3-chloro-4-bromophenyl)-N'-methyl-N'-methoxy-urea(chlorbromuron), a herbicidal substance,
N-(3-fluoro-4-bromophenyl)-N',N'-dimethyl-urea, a herbicidal substance,
N-(3-fluoro-4-chlorophenyl)-N',N'-dimethyl-urea, a herbicidal substance,
N-(3-fluoro-4-chlorophenyl)-N'-methyl-N'-methoxy-urea, a herbicidal substance,
N-(3-fluoro-4-iodophenyl)-N'-methyl-N'-methoxy-urea, a herbicidal substance,
N-(4-chlorophenyl)-N'-(3-methyl-4-chlorophenyl)-urea, a herbicidal substance,
N-(4-nitrophenyl)-N'-(3'-pyridylmethyl)-urea(pyrinuron), a rodenticidal substance,
N-(4-chlorophenyl)-N'-(3,4-dichlorophenyl)-urea(triclocarban), a bacteriostatic agent,
N-(4-nitrophenyl)-N'-(4-nitrophenyl)-urea(nicarbazin), a coccidiostatic agent, and
N-(4-chlorophenyl)-N'-(3-trifluoromethyl-4-chlorophenyl)-urea(cloflucarban), an antiseptic agent.

The most widely applied methods for the preparation of the compounds having the general formula (I) are based on the reaction of isocyanates and amine derivatives. According to one of these methods isocyanates of the general formula Aryl—NCO are reacted with amines of the general formula $NHR^1R^2$, whereas according to another method isocyanates of the general formula $R^1$—NCO and amines of the general formula Aryl—$NH_2$ are applied as reactants. In this latter method compounds of the general formula (I) wherein $R^2$ is hydrogen are formed. A general description of these reactions can be found in Houben-Weyl: Methoden der organischen Chemie (Georg Thieme Verlag, Stuttgart, 1952, Vol. VIII, pp. 154–156).

The isocyanates applied as starting substances in the above methods are preapred generally by reacting the appropriate amines with phosgene or by subjecting the appropriate carbamates or urea derivatives to thermal decomposition (see Houben-Weyl: Methoden der organischen Chemie; Georg Thieme Verlag, Stuttgart, 1952, Vol. VIII, pp. 119–128).

It is well known that phosgene is highly detrimental to health, thus reactions utilizing phosgene should be performed under keeping specific security measures. It is a further disadvantage that the reaction involves the formation of hydrochloric acid in great amounts, which is difficult to remove and causes serious corrosion problems. The methods of preparing isocyanates by thermal decomposition are very expensive because of their high demands on material and energy. Thus the preparation of isocyanates, applied as starting materials in the synthesis of the urea derivatives of the general formula (I), is cumbersome, sophisticated and expensive, and the reaction cannot be performed economically on industrial scale. It is a further disadvantage that isocyanates, owing to their high reactivity, are instable compounds and can be stored for a limited period, sometimes for some days only. Thus e.g. 4-nitrophenylisocyanate undergoes water addition and subsequent condensation upon storage, whereby dimers, trimers and other oligomers are formed which cannot be reacted with amines in the subsequent step (see Houbed-Weyl: Methoden der organischen Chemie, Georg Thieme Verlag, Stuttgart, 1952, Vol. VIII, p. 159).

It is also known that urea derivatives can be prepared by reacting carbamates with appropriate primary or secondary amines in the presence of a tertiary amine catalysts [see e.g. J. Am. Chem. Soc. 76, 4458–4463 (1954)]. According to the literature, however, only phenyl carbamates and substituted phenyl carbamates are reactive enough (Houben-Weyl: Methoden der organischen Chemie, Georg Thieme Verlag, Stuttgart, 1952, Vol. VIII, pp. 161–162), and if lower alkyl carbamates, which are far more easy to prepare than the respective phenyl or substituted phenyl esters, are applied as starting substances, the reaction proceeds with very low yields and requires an extremely long time, or even no reaction occurs at all. Therefore in large-scale operations lower alkyl carbamates are utilized to prepare urea derivatives only by subjecting them first to thermal decomposition, which requires much energy, and then reacting the resulting isocyanates with amines.

It follows from the above that none of the hitherto known methods of producing urea derivatives is completely satisfactory with respect to reaction time, availability of starting substances and security of operations.

The invention aims at the elaboration of a new method for the preparation of urea derivatives having the general formula (I), which requires easily available starting substances, provides the end-products with high yields within a short time, and does not apply substances detrimental to health.

The invention is based on the recognition that lower alkyl carbamates can be converted into the respective urea derivatives directly, i.e. without converting them first into isocyanates, within a short time and with high yields if they are reacted with the respective amines in the presence of higher tertiary alkylamine catalysts instead of the lower tertiary amines (most frequently triethylamine or pyridine) utilized so far. It has also been observed that if phenyl or substituted phenyl carbamates are applied as starting substances in the above reaction and the lower tertiary amine catalyst is replaced by a higher tertiary alkylamine, the required end-products are obtained with higher yields. In these latter instances the yield increases sometimes to the double or more; thus e.g. N-(4-cyanophenyl)-N'-(3-pyridylmethyl)-urea can be obtained with a yield of 85 to 90% instead of 43% attained when operating as described in Example 2 of the Hungarian patent specification No. 168,295.

Based on the above, the invention relates to a new method of preparing an urea derivative of the general formula (I),

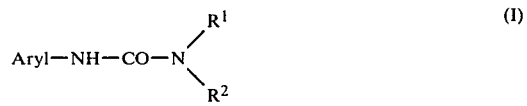

wherein Aryl, $R^1$ and $R^2$ are as defined above, by reacting a carbamate of the general formula (II) with an amine of the general formula (III), $$R^1R^2N-CO-X \quad (II)$$

or a carbamate of the general formula (IV) with an amine of the general formula (V), $$Aryl-NH-CO-X \quad (IV)$$

$$R^1R^2NH \quad (V)$$

wherein $R^1$, $R^2$ and Aryl are as defined above and X is a lower alkoxy, phenoxy or substituted phenoxy group, in the presence of a tertiary amine catalyst. According to the invention a tertiary alkylamine containing altogether at least 6 carbon atoms and minimum one alkyl chain with at least 4 carbon atoms or a mixture of such tertiary alkylamines is applied as catalyst.

As it appears from the above definition, di($C_{1-3}$alkyl)-butylamines can also be applied as tertiary alkylamine catalysts, it is more preferred, however, to perform the reaction in the presence of a tertiary amine wherein the highest alkyl chain contains at least 8, particularly at least 12 carbon atoms. The other two alkyl groups attached to the nitrogen atom may be lower alkyl groups, such as methyl or ethyl group. According to our experiences the catalytic effect of the tertiary alkylamines varies generally parallel with the carbon atom number of the highest alkyl chain, i.e. the greater is the carbon atom number of the highest chain, the shorter is the reaction time and the higher is the yield of the required urea derivative. Of the tertiary alkylamine catalysts the following compounds are particularly preferred: trioctylamine, N,N-dimethyl-n-octylamine, N,N-dimethyl-n-dodecylamine, N,N-dimethyl-n-hexadecylamine and the respective N,N-diethyl or N-methyl-N-ethyl compounds. These substances are easily available on the market.

As mentioned above, mixtures of higher tertiary alkylamines can also be applied as catalysts in the process of the invention. From economical aspects it is preferred to utilize such mixtures of technical quality in large-scale operations, since these mixtures are far less expensive than the pure tertiary amines without any appreciable decrease in their catalytic activity. Of the mixtures of higher tertiary alkylamines e.g. the products sold by the firm Hoechst A. G. under the trade name "Genamin" as well as those sold by the firm Akzo under the trade name "Armeens" are to be mentioned.

The term "lower alkoxy" used in connection with substituent X refers to $C_{1-4}$ alkoxy groups, such as methoxy, ethoxy, etc. The term "substituted phenoxy" used in connection with group X refers to phenoxy groups which bear one or more substituent(s) inert under the reaction conditions, such as halogen atoms or alkyl, alkoxy, trihaloalkyl and/or nitro groups. Particularly preferred representatives of the substituents attached to the phenoxy group are electron-attracting groups (e.g. halogen atoms, nitro group), since the phenoxycarbamates with electron-attracting substituents on the aromatic ring are particularly reactive under the conditions according to the invention.

According to the invention the lower aklyl carbamates, regarded so far as substances which cannot be used for the direct industrial preparaton of urea derivatives, can be converted directly into the respective ureas within some hours generally with yields of 80% or more. If phenoxy or substituted phenoxy carbamates are applied as starting substances, the end-product may be obtained with almost quantitative yields in a fast reaction.

The starting substances (i.e. the carbamates and the primary or secondary amines) are applied preferably in practically equimolar amounts, although any of the reactants may also be used in excess. The higher tertiary alkylamine catalyst is added to the mixture in an amount of 0.05 to 2 moles, preferably 0.5 to 1.2 moles, calculated for 1 mole of the starting substance present in the lower molar amount. When a mixture of higher tertiary amines is applied as catalyst, this ratio relates to the total amount of tertiary amines.

The reaction is performed generally in an inert solvent medium, such as benzene, toluene or xylene, preferably under boiling the reaction mixture. The excess of the higher tertiary alkylamine may also serve as solvent, or sometimes the reaction may also be performed in the absence of solvent or diluent.

The urea derivatives of the general formula (I) are generally sparingly soluble in the reaction medium and separate as solids upon cooling the mixture. In such instances the end-products can be separated easily by filtration or centrifugation. The resulting mother liquor, which contains solvent, higher tertiary alkylamine catalyst, minor amounts of unreacted starting substances and dissolved end-product, can be utilized repeatedly as reaction medium for further reaction steps. Thereby the specific demand on reactants and catalyst can be decreased substantially. In such instances it is preferred to apply the starting substances in equimolar ratio in order to avoid the accumulation of one of the reactants in the mixture. When the mother liquor is recycled the yield generally increases, since after the first step no further losses arise owing to the dissolution of the end-product.

It is also preferred to allow distillation of the mixture under boiling, removing thereby the spures of water and the alcohol which forms in the reaction. In this instance it is not necessary to apply anhydrous starting substances and dry solvents.

The end-products which do not precipitate from the reaction mixture upon cooling can be separated from the mixture by known methods, such as evaporation, precipitation with non-solvents, etc. In certain fields of application, thus if the urea derivatives are to be used in the agriculture e.g. as pesticidal agents, it is not always necessary to separate them from the reaction mixture, since this mixture can be applied directly in the preparation of agrochemical compositions (such as spray solutions, impregnated granules, etc.) by admixing it with the necessary additives, if required. The mother liquors obtained after the separation of the solid endproducts, which contain certain amount of dissolved urea derivatives, can also be applied for the same purpose. Depending on the field of final utilization, the separated crude urea derivatives can be applied either as such or after purification.

The process of the invention can equally be applied for the preparation of symmetrically and asymmetrically substituted urea derivatives.

The process of the invention is elucidated in detail by the aid of the following non-limiting Examples. It should be noted here that the primary aim of the examples is to illustrate the wide applicability of the new method, thus no effort was made to attain the optimum result in all of the reactions. As an example, the number of recycling the mother liquors given in the examples does not represent the maximum possible value. According to our experiences the mother liquors can be recycled at least 10 times.

The layer chromatographic analyses referred to in the examples were performed on Merck Kieselgel 60 $F_{254}$ plates. The melting points are uncorrected values.

EXAMPLE 1

Preparation of
N-(4-nitrophenyl)-N'-(3-pyridylmethyl)-urea 4.22 g (0.02 mole) of ethyl N-(4-nitrophenyl)carbamate, 1.80 g (0.0167 mole) of 3-aminomethyl-pyridine and 3.18 g (0.0173 mole) of tributylamine are dissolved in 25 ml of dry toluene, and the mixture is boiled for 5 hours. The separated product is filtered off, washed twice with 10 ml of acetone, each, and dried. 4.33 g (85.1%) of N-(4-nitrophenyl)-N'-(3-pyridylmethyl)-urea are obtained; m.p.: 222°–224° C. (the authentic sample melts at 223°–225° C.).

The above reaction is repeated with the difference that 1.72 g (0.0175 mole) of triethylamine are applied as catalyst. The end-product starts to separate only after about 4 hours of boiling. The mixture is boiled for 36 hours, thereafter the separated product is filtered off and washed twice with 10 ml of acetone, each. 3.3 g (64.9%) of N-(4-nitrophenyl)-N'-(3-pyridylmethyl)urea are obtained; m.p.: 222°–224° C.

EXAMPLE 2

Preparation of
N-(4-nitrophenyl)-N'-(3-pyridylmethyl)-urea 196.13 g (1 mole) of methyl N-(4-nitrophenyl)-carbamate, 108.14 g (1 mole) of 3-aminomethyl-pyridine and 106.7 g (0.5 mole) of N,N-dimethyl-n-dodecylamine are dissolved in 3 liters of xylene. The reaction mixture is refluxed, and the spures of water present are removed from the mixture together with the alcohol formed in a Dean-Stark trap. The end-product starts to separate from the mixture within 15–20 minutes from the beginning of boiling. The mixture is boiled for 4 hours, thereafter the suspension is filtered at about 100° to 110° C. The filter cake is washed twice with 100 ml of hot xylene, each, and with a small amount of acetone, and then dried in vacuo. 218.6 g (80.3%) of N-(4-nitrophenyl)-

N'-(3-pyridylmethyl)-urea are obtained; m.p.: 221°-223° C.

EXAMPLE 3

Preparation of N-(4-nitrophenyl)-N'-(3-pyridylmethyl)-urea

One proceeds as described in Example 2 with the difference that 0.5 mole of N,N-dimethyl-n-hexadecylamine is applied as catalyst. 240.67 g (88.4%) of N-(4-nitrophenyl)-N'-(3-pyridylmethyl)-urea are obtained; m.p.: 222°-224° C.

EXAMPLE 4

Preparation of N-(4-nitrophenyl)-N'-(3-pyridylmethyl)-urea

A mixture of 5.88 g (0.03 mole) of methyl N-(4-nitrophenyl)-carbamate, 2.70 g (0.025 mole) of 3-aminomethyl-pyridine, 9.6 ml of Gemanin CS 302D (a mixture of N,N-dimethyl-$C_{10-18}$ alkylamines sold by the firm Hoechst AG) and 50 ml of xylene is filled into a flask equipped with a 20 cm Vigreux column and a Dean-Stark trap, and the mixture is boiled for 2 hours. During this period 6 ml of a mixture of water, methanol and xylene accumulate in the trap. The mixture is filtered when hot, the crystalline end-product is washed twice with 5 ml of hot xylene, each, and then with a few amount of acetone and dried. 6.0 g (88.2%) of N-(4-nitrophenyl)-N'-(3-pyridylmethyl)-urea are obtained; m.p.: 223°-225° C.

EXAMPLE 5

Preparation of N-(4-nitrophenyl)-N'-(3-pyridylmethyl)-urea 11.77 g (0.06 mole) of methyl N-(4-nitrophenyl)carbamate, 5.4 g (0.05 mole) of 3-aminomethyl-pyridine, 18.7 g (0.065 mole) of Genamin SH 302 D (a mixture of N,N-dimethyl-$C_{16-18}$ alkylamines sold by the firm Hoechst AG) and 200 ml of toluene are introduced into the apparatus described in Example 4, and the mixture is boiled for 4 hours. During this period 15 ml of a mixture of water, methanol and toluene accumulate in the trap. The separated solid is filtered off, washed twice with 10 ml of hot toluene, and the resulting mixture is used as reaction medium in the above reaction. The mother liquor is recycled 10 times. The results of the individual cycles are summarized in Table 1.

TABLE 1

| Number of the cycle | End - product | | |
|---|---|---|---|
| | Weight, g | M.p. °C. | Yield, % |
| 1 | 10.85 | 221–223 | 79.72 |
| 2 | 12.95 | 223–225 | 95.15 |
| 3 | 11.95 | 222–224 | 87.80 |
| 4 | 10.65 | 221–223 | 78.25 |
| 5 | 11.00 | 222–224 | 80.82 |
| 6 | 11.82 | 224–225 | 86.84 |
| 7 | 12.65 | 224–226 | 92.94 |
| 8 | 10.50 | 223–225 | 77.14 |
| 9 | 11.00 | 222–224 | 80.82 |
| 10 | 13.28 | 224–226 | 97.57 |
| average | 11.66 | | 85.70 |

EXAMPLE 6

Preparation of N,N'-bis(4-nitrophenyl)-urea 9.81 g (50 mmoles) of methyl N-(4-nitrophenyl)carbamate, 6.9 g (50 mmoles) of 4-nitroaniline, 140 ml of xylene and 11.8 g (about 50 mmoles) of Genamin CS 302 D (a mixture of N,N-dimethyl-$C_{10-18}$ alkylamines sold by the firm Hoechst AG) are introduced into a flask equipped with a reflux condenser, and the mixture is boiled. The yellow crystals of the end-product appear already in the 3rd minute of boiling, and the amount of the crystalline precipitate rapidly increases. After 0.5 hours of boiling the thick, orange crystal suspension is filtered in vacuo when hot, the filter cake is washed twich with 20 ml of hot xylene, each, and then with acetone, finally the product is dried in vacuo. 12.78 g (85.2%) of N,N'-bis(4-nitrophenyl)-urea are obtained. The product is uniform when examined by layer chromatography utilizing a 3:1 mixture of n-hexane and acetone as solvent, and the chromatographic appearance of the product is identical with that of the authentic sample.

EXAMPLE 7

Preparation of N,N'-bis(4-nitrophenyl)-urea

One proceeds as described in Example 6 with the difference that a distillating column is attached to the flask, the mixture is maintained in gentle boiling and methanol is removed continuously from the mixture. After 2 hours of reaction the end-product is filtered off, 50 mmoles of methyl N-(4-nitrophenyl)-carbamate and 50 mmoles of 4-nitroaniline are added to the filtrate, and the reaction is repeated. The results of four subsequent cycles are summarized in Table 2.

TABLE 2

| Number of the cycle | End - product | | |
|---|---|---|---|
| | Weight, g | Yield, % | Chromatographic appearance |
| 1 | 13.36 | 89.1 | uniform |
| 2 | 14.30 | 95.3 | uniform |
| 3 | 13.58 | 90.5 | uniform |
| 4 | 14.75 | 98.3 | uniform |

Remark:
The quality of the end-product cannot be characterized appropriately on the basis of its melting point, since the compound starts to sublime directly after melting.

EXAMPLE 8

Preparation of N-(4-chlorophenyl)-carbamoylmorpholine

A mixture of 9.28 g (50 mmoles) of methyl N-(4-chlorophenyl)-carbamate, 4.36 g (50 mmoles) of morpholine, 100 ml of xylene and 10.6 g (50 mmoles) of N,N-dimethyltetradecylamine is boiled gently for 6 hours, and methanol is continuously removed from the mixture by distillation. Thereafter heating is stopped and the mixture is allowed to cool and stand overnight. The separated crystals are filtered off and dried. 9.1 g (75.6%) of N-(4-chlorophenyl)-carbamoyl-morpholine are obtained; m.p.: 196°-200° C. (the authentic sample melts at 196°-200° C.).

EXAMPLE 9

Preparation of N-(4-chlorophenyl)-N'-(3,4-dichlorophenyl)-urea

A mixture of 4.61 g (25 mmoles) of methyl N-(4-chlorophenyl)-carbamate, 4.07 g (25 mmoles) of 3,4-dichloroaniline, 100 ml of toluene and 4.7 g (25 mmoles) of N,N-dimethyl-dodecylamine is reacted for 20 hours as described in Example 8, and then the mixture is allowed to cool. 4.60 g (58.4%) of N-(4-chlorophenyl)-N'-(3,4-dichlorophenyl)-urea separate from the mixture as a crystalline substance.

EXAMPLE 10

Preparation of N-(3-dichlorophenyl)-carbamoylmorpholine

A mixture of 5.50 g (25 mmoles) of methyl N-(3,4-dichlorophenyl)-carbamate, 2.18 g (25 mmoles) of morpholine, 100 ml of xylene and 4.7 g (25 mmoles) of N,N-dimethyl-dodecylamine is reacted for 12 hours as described in Example 8. The crystalline substance which separates upon cooling is filtered off, 25 mmoles of methyl N-(3,4-dichlorophenyl)-carbamate and 25 mmoles of morpholine are added to the filtrate, and the reaction is repeated. In the first reaction 5.0 (72.7%) of N-(3,4-dichlorophenyl)carbamoyl-morpholine are obtained, whereas 6.35 g (92.3%) of the same compound are separated in the second reaction. Both compound fractions melt at 152°–155° C. (the authentic sample melts at 157°–158° C.).

The above reaction is repeated so that 25 mmoles of triethylamine are added to the mixture instead of N,N-dimethyl-dodecylamine. 3.05 g (44.3%) of the desired end-product are obtained after 24 hours of reaction.

EXAMPLE 11

Preparation of N-(3,4-dichlorophenyl)-N'-methyl-N'-butyl-urea

A mixture of 5.50 g (25 mmoles) of methyl N-(3,4-dichlorophenyl)-carbamate, 2.18 g (25 mmoles) of N-butylmethylamine, 4.7 g (25 mmoles) of N,N-dimethyl-dodecylamine and 100 ml of light petrol is reacted for 3 hours as described in Example 8. The separated solid is filtered off, 25 mmoles of methyl N-(3,4-dichlorophenyl)carbamate and 2.18 g (25 mmoles) of N-butyl-methylamine are added to the filtrate, and the reaction is repeated. In the first reaction 3.70 g (53.8%) of N-(3,4-dichlorophenyl)-N'-methyl-N'-butyl-urea are obtained, whereas 5.05 g (73.4%) of the same compound are separated in the second reaction. Both compound fractions melt at 108°–110° C. (the authentic sample melts at 116°–117° C.).

EXAMPLE 12

Preparation of N-(3,4-dichlorophenyl)-N'-methyl-N'-butyl-urea

One proceeds as described in Example 11 with the difference that 100 ml of xylene are applied as solvent, and the progress of the reaction is monitored by layer chromatography. When the reaction has proceeded to about 90%, as indicated by the chromatogram, the mixture is evaporated in vacuo. A yellowish, viscous residue is obtained, which is well soluble in common organic solvents, such as acetone or methyl-ethyl ketone, and can be applied in the preparation of a herbicidal spray solution.

EXAMPLE 13

Preparation of N-(4-chlorophenyl)-N',N'-dimethyl-urea

A mixture of 12.8 g (0.1 mole) of 4-chloroaniline, 10.3 g (0.1 mole) of methyl N,N-dimethyl-carbamate, 20 ml of dimethyl-hexadecylamine and 100 ml of high boiling petroleum fractions (bp.: 160°–180° C.) is reacted as described in Example 12. When the reaction has proceeded to about 90%, as indicated by the chromatogram, the reaction is terminated. A solution of N-(4-chlorophenyl)-N',N'-dimethyl-urea (monuron) is obtained, which can be applied directly in the preparation of herbicidal compositions, such as spray liquids or impregnated granules.

EXAMPLE 14

Preparation of N-(4-chlorophenyl)-N',N'-dimethylurea 4.64 g (0.025 mole) of methyl N-(4-chlorophenyl)carbamate and 21.3 ml of Genamin LA 302 D (a mixture of N,N-dimethyl-$C_{12-14}$ alkylamines sold by the firm Hoechst AG) are introduced into a 100 ml flask equipped with a distillating column. The mixture is heated to 150°–160° C., and gaseous dimethylamine is introduced into the mixture. In the final stage of the reaction the mixture is heated above 160° C. in order to remove methanol. The complete reaction time is of about 2 hours.

The resulting yellowish brown solution is allowed to cool, and the almost white crystalline precipitate is collected by filtration. The precipitate is washed thrice with 10 ml of n-hexane, each, and then dried. The filtrate is combined with the wash, and the resulting mixture is applied as reaction medium in the next cycle. In the next cycle 4.64 g of the above carbamate are introduced into the reaction medium, and the mixture is heated under the introduction of gaseous dimethylamine. n-Hexane, applied as washing agent in the previous cycle, distils first, which is collected separately and applied as washing agent again.

The combined mother liquor and wash are recycled 10 times. The results of the individual cycles are summarized in Table 3.

TABLE 3

| Number of the cycle | End - product Weight, g | M.p. °C. | Yield, % |
|---|---|---|---|
| 1 | 2.70 | 168–171 | 54.33 |
| 2 | 3.05 | 169–171 | 61.36 |
| 3 | 4.20 | 170–172 | 84.51 |
| 4 | 4.50 | 169–171 | 90.54 |
| 5 | 4.10 | 167–169 | 82.49 |
| 6 | 3.50 | 167–169 | 70.42 |
| 7 | 4.50 | 168–169 | 90.54 |
| 8 | 3.95 | 172–173 | 79.48 |
| 9 | 3.75 | 172–173 | 75.45 |
| 10 | 4.55 | 168–169 | 91.55 |
| average | 3.88 | | 78.07 |

Remark:
The melting point of N—(4-chlorophenyl)-N',N'—dimethyl-urea (monuron), reported in the literature, is 174–175° C.

EXAMPLE 15

Preparation of N-phenyl-N',N'-dimethyl-urea

One proceeds as described in Example 14 with the difference that 3.78 g (0.025 mole) of methyl N-phenyl-carbamate are applied as starting substance, and the mixture is heated at 140°–180° C. for 1.5 hours. The combined mother liquor and wash are recycled 8 times. The results of the individual cycles are summarized in Table 4.

TABLE 4

| Number of the cycle | End - product Weight, g | M.p. °C. | Yield, % |
|---|---|---|---|
| 1 | 2.10 | 127–130 | 51.20 |
| 2 | 3.41 | 124–127 | 83.17 |
| 3 | 3.85 | 125–128 | 93.90 |
| 4 | 3.75 | 124–126 | 91.46 |
| 5 | 1.87 | 131–133 | 45.61 |
| 6 | 4.95 | 124–127 | 120.73 |
| 7 | 3.05 | 122–126 | 74.40 |
| 8 | 3.60 | 122–126 | 87.80 |

TABLE 4-continued

| Number of | End - product | | |
|---|---|---|---|
| the cycle | Weight, g | M.p. °C. | Yield, % |
| average | 3.32 | | 81.03 |

Remark:
The melting point of N—phenyl-N',N'—dimethyl-urea (phenuron), reported in the literature, is 133–134° C.

EXAMPLE 16

Preparation of
N-(3,4-dichlorophenyl)-N'-methoxy-N'-methyl-urea 5.5 g (0.025 mole) of methyl N-(3,4-dichlorophenyl)-carbamate are dissolved in 23 ml (about 0.075 mole) of Genamin LA 302D (a mixture of N,N-dimethyl-$C_{12-14}$ alkylamines sold by the firm Hoechst AG) under stirring and heating. The mixture is maintained at a temperature of about 200° C. and 2.3 g (0.0375 mole) of gaseous methoxymethylamine are bubbled through the mixture within about 3 hours. The progress of the reaction is monitored by layer chromatography, and is also checked by measuring the temperature of the vapours leaving the mixture. When the conversion ratio reached about 90%, the reaction is terminated. A solution of N-(3-dichlorophehyl)-N'-methoxy-N'-methyl-urea (linuron) is obtained. This solution can be diluted easily with conventional organic solvents, such as acetone or methylethyl-ketone, and can be applied then directly for the preparation of herbicidal compositions, such as spray liquids or impregnated granulates.

What we claim is:

1. A process for the preparation of N-aryl-N'-(mono- or disubstituted)-urea derivatives having the formula (I),

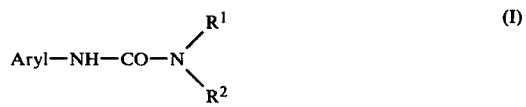

wherein
Aryl is an optionally substituted phenyl group, and $R^1$ and $R^2$ each stand for an optionally substituted alkyl, cycloalkyl, alkoxy or phenyl group, or $R^1$ and $R^2$ may form, together with the adjacent nitrogen atom, a nitrogen-containing heterocyclic group which may contain a further hetero atom, or one of $R^1$ and $R^2$ may also stand for hydrogen, with the proviso that if one of $R^1$ and $R^2$ is an optionally substituted phenyl group, the other may represent only hydrogen atom or an optionally substituted alkyl or alkoxy group,
by reacting a carbamate of the formula (II) with an amine of the formula (III),

or a carbamate of the general formula (IV) with an amine of the general formula (V),

wherein $R^1$, $R^2$ and Aryl are as defined above and X is a lower alkoxy, phenoxy or substituted phenoxy group, in the presence of a tertiary amine catalyst, characterized in that a tertiary alkylamine containing altogether at least 6 carbon atoms and minimum one alkyl chain with at least 4 carbon atoms or a mixture of such tertiary alkylamines is applied as catalyst.

2. A process as set forth in claim 1, characterized in that a tertiary alkylamine containing at least one alkyl chain with at least 8 carbon atoms or a mixture of such tertiary alkylamines is applied as catalyst.

3. A process as set forth in claim 1 or 2, characterized in that the tertiary alkylamine catalyst is applied in an amount of 0.05–2 moles calculated for 1 mole of the reactant present in lower molar amount.

4. A process as set forth in any of claims 1 or 2, characterized in that the tertiary alkylamine catalyst is applied in an amount of 0.5–1.2 moles calculated for 1 mole of the reactant present in lower molar amount.

5. A process as set forth in claim 1 or 2, characterized in that the tertiary alkyl amine catalyst is selected from the group consisting of N,N-dimethyl-n-octylamine, N,N-dimethyl-n-dodecylamine, N,N-dimethyl-n-hexadecylamine, N,N-diethyl-n-oxtylamine, N,N-diethyl-n-dodecylamine, N,N-diethyl-n-hexadecyl, N-methyl-N-ethyl-n-octylamine, N-methyl-N-ethyl-n-dodecylamine, N-methyl-N-ethyl-n-hexadecylamine or mixtures thereof.

* * * * *